United States Patent
Hanson et al.

(10) Patent No.: US 6,962,670 B1
(45) Date of Patent: Nov. 8, 2005

(54) DETERMINATION OF LAYER THICKNESS OR NON-UNIFORMITY OF LAYER THICKNESS BASED ON FLUOROPHORE ADDITIVES

(75) Inventors: Scott Arnold Hanson, Longview, TX (US); Gregory Wayne Nelson, Kingsport, TN (US); Michael Eugene Donelson, Gray, TN (US)

(73) Assignee: Eastman Chemical Company, Kingsport, TN (US)

(*) Notice: Subject to any disclaimer, the term of this patent is extended or adjusted under 35 U.S.C. 154(b) by 698 days.

(21) Appl. No.: 09/640,318

(22) Filed: Aug. 16, 2000

(51) Int. Cl.⁷ .................... C09K 11/00; G01B 15/02
(52) U.S. Cl. ............... 264/21; 264/40.1; 264/40.6; 264/454; 264/464; 264/478
(58) Field of Search .................. 264/21, 406, 40.1, 264/454, 464, 478, 40.6

(56) References Cited

U.S. PATENT DOCUMENTS

| | | |
|---|---|---|
| 3,709,896 A | 1/1973 | Frischkorn et al. |
| 3,843,479 A | 10/1974 | Matsunami et al. |
| 3,946,089 A | 3/1976 | Furukawa et al. |
| 4,133,802 A | 1/1979 | Hachiboshi et al. |
| 4,305,816 A | 12/1981 | Flood et al. |
| 4,477,521 A * | 10/1984 | Lehmann et al. ........... 428/336 |
| 4,691,231 A | 9/1987 | Fitzmorris et al. |
| 4,803,241 A | 2/1989 | Weaver et al. |
| 4,882,412 A | 11/1989 | Weaver et al. |
| 4,892,922 A | 1/1990 | Weaver et al. |
| 4,892,923 A | 1/1990 | Weaver et al. |
| 4,919,855 A * | 4/1990 | Thomas ....................... 264/21 |
| 4,956,558 A | 9/1990 | Batishko et al. |
| 5,030,708 A | 7/1991 | Krutak et al. |
| 5,091,501 A | 2/1992 | Weaver et al. |
| 5,106,942 A | 4/1992 | Krutak et al. |
| 5,155,443 A | 10/1992 | Baker |
| 5,201,921 A | 4/1993 | Luttermann et al. |
| 5,274,072 A | 12/1993 | Weaver et al. |
| 5,292,855 A | 3/1994 | Krutak et al. |
| 5,336,714 A | 8/1994 | Krutak et al. |
| 5,397,819 A | 3/1995 | Krutak et al. |
| 5,423,432 A | 6/1995 | Krutak et al. |
| 5,461,136 A | 10/1995 | Krutak et al. |
| 5,491,204 A | 2/1996 | Nugent, Jr. et al. |
| 5,498,455 A | 3/1996 | Roberts |
| 5,553,714 A | 9/1996 | Cushman et al. |

(Continued)

FOREIGN PATENT DOCUMENTS

DE    29 07 620 A    8/1980

(Continued)

OTHER PUBLICATIONS

Kirk-Othmer Encyclopedia of Chemical Technology, third edition, vol. 18, pp 479-494.

(Continued)

*Primary Examiner*—Suzanne E. McDowell
(74) *Attorney, Agent, or Firm*—Eric D. Middlemas; Bernard J. Graves, Jr.

(57) ABSTRACT

The invention provides a method for measuring the thickness, or non-uniformity of thickness, of one or more layers of a film or article such as a preform. At least one layer contains a known concentration and a substantially uniform distribution of fluorophores. The fluorophores are added to the one or more layers in sufficient quantity to impart fluorescence capable of detection by a detector when exposed to electromagnetic radiation at absorbing wavelengths. The layers of the invention may be made from polymeric material, non-polymeric material, or combinations thereof.

32 Claims, 6 Drawing Sheets

U.S. PATENT DOCUMENTS

| | | |
|---|---|---|
| 5,558,233 A | 9/1996 | Dimmick et al. |
| 5,614,008 A | 3/1997 | Escano et al. |
| 5,637,365 A | 6/1997 | Carlblom |
| 5,650,455 A | 7/1997 | Atkins et al. |
| 5,652,034 A | 7/1997 | Seiner |
| 5,703,229 A | 12/1997 | Krutak et al. |
| 5,728,439 A | 3/1998 | Carlblom et al. |
| 5,762,698 A | 6/1998 | Atkins et al. |
| 5,783,307 A | 7/1998 | Fagerburg et al. |
| 5,804,447 A | 9/1998 | Albert et al. |
| 5,840,825 A | 11/1998 | Carlblom et al. |
| 5,902,643 A | 5/1999 | Carlblom et al. |
| 6,682,810 B1 * | 1/2004 | Jones et al. ............... 428/323 |

FOREIGN PATENT DOCUMENTS

| | | |
|---|---|---|
| EP | 0 336 029 | 10/1989 |
| JP | 57535/75 B | 3/1975 |
| JP | 10196/75 B | 4/1975 |
| WO | WO 98 29709 A | 7/1998 |
| WO | WO 99 15881 A | 4/1999 |
| WO | WO 00 04340 A | 1/2000 |
| WO | PCT/US99/28220 A1 | 6/2000 |
| WO | PCT/US99/28981 A1 | 6/2000 |

OTHER PUBLICATIONS

R. Gachter and H. Mueller, Editors, Plastics Additives Handbook, Hansu Publishers, New York, 1985, pp 507-533; 729-741.

Chapter 8, vol. 1 of *Fluorescence Microscopy* by F. D. Roast and published by Cambridge University Press in 1992.

* cited by examiner

DETERMINATION OF LAYER THICKNESS OR NON-UNIFORMITY OF LAYER THICKNESS BASED ON FLUOROPHORE ADDITIVES

FIELD OF THE INVENTION

The invention relates to the determination of thickness, or non-uniformity of thickness, of one or more layers. The layers comprise polymeric materials, nonpolymeric materials, or combinations thereof. The invention employs fluorophores as compositional additives to at least one layer. The fluorophores are exposed to electromagnetic radiation and the resultant fluorescence is used a measure of the thickness, or non-uniformity of thickness, of the one or more layers.

BACKGROUND OF THE INVENTION

Polymers are commonly extruded or injection molded to make films, sheets, preforms, and other molded articles useful for a wide range of applications including containers such as bottles and cups; wrappers for packaging; various displays; signs; and multiple other products. Often additional layers are coextruded with a base layer to improve certain properties. Other times additional layers are coated onto a base layer. Such additional layers can be made from a different material than the base layer to improve particular properties such as barrier properties which limit migration of various liquids or gases. Alternatively, the additional layers could be made substantially of the same resin as the base layer, but contain an additive designed to improve certain properties, such as the addition of a UV absorber to minimize degradation of the base material. Control of the layer thickness is often critical in terms of performance and cost. A major problem in the industry is the measurement of the thickness of polymer layers on line during the extrusion, coating, injection molding, or other manufacturing process.

The need for thickness control is particularly important for multi-layer preforms used to make containers, such as bottles for beer, soda, or other carbonated beverages. The preform is typically blow molded to make the container. Such multi-layer plastic containers often contain a thin layer which provides a barrier against migration of gases such as carbon dioxide or oxygen. Because the layer is thin, it is critical that the layer be uniform in thickness; a non-uniformity such as a thin section or a pinhole could substantially degrade the barrier properties—significantly decreasing the performance of the resultant container.

Measurement of the thickness of polymer layers on line has been done using optical transmission techniques, whereby light from a UV, visible, or IR source is passed through the sample, and a component of the layer being measured selectively absorbs some of the light. U.S. Pat. No. 4,691,231 discloses a method and an apparatus for inspecting the sidewalls of containers such as returnable soft drink or beer bottles. The bottles are illuminated with front lighting and back lighting. Reflection and transmission of the light is recorded by six different video scan fields. The signals are examined to determine the presence of dirt, other foreign material, scuffs or other defects on the sidewalls of the bottles.

This technique is not useful when the structure contains opaque material, and the incident beam of light is blocked from passing through the sample across the wavelengths of interest.

Measurement of layers on-line has also been done using interference techniques, whereby light is passed through the sample, and the light is reflected from the various interfaces. The reflections can constructively or destructively interfere depending on the index of refraction of the layers, and the thickness of the layers. This technique is extremely difficult in practice because the difference in index of refraction at the interface between the layers must be great enough to reflect light, the interface must be very sharp (no interdiffusion between the layers) and the thickness of the layers must be very uniform over the sample area measured. Such conditions are difficult to achieve.

Measurements of wall thickness of a container has been performed using optical transmission or reflection techniques wherein a container wall is illuminated with front and back light. Reflected light and transmitted light are imaged and converted to a measurement of wall thickness.

Other techniques for measuring wall thickness of a container include using the dielectric properties of the container wall in conjunction with a capacitance sensor. U.S. Pat. Nos. 5,155,443 and 5,558,233 provide methods and apparatuses for determining the wall thickness of containers composed of a dielectric material.

In addition to the above techniques for measuring thickness, other information about plastic layers and containers has been obtained by adding fluorescent dyes to precursor polymer compositions. U.S. Pat. No. 5,201,921 provides a process for rendering a plastic identifiable by adding 5 to 10,000 ppb of a fluorescent marker to the plastic during or after its manufacture. The patent describes the use of the process for marking, identifying, and sorting plastic bottles. The process can be used for sorting plastic bottles in preparation for recycling.

U.S. Pat. Nos. 5,292,855; 5,336,714; & 5,423,432 provide water-dissipatable, sulfo-containing polyesters and polyesteramides having copolymerized therein thermally stable near infrared fluorophoric compounds. The polymers can be used to create a coating or ink which may be used to mark articles for the purpose of detection or identification.

U.S. Pat. Nos. 5,397,819; 5,461,136; 5,553,714; & 5,703,229 provide novel near infrared (NIR) fluorophores. The fluorophores are phthalocyanine and naphthalocyanine derivatives which are covalently bonded to substituted silicon and aluminum compounds which fluoresce in the near infrared range. The patents also provide a method using the fluorophores to mark thermoplastic compositions and containers made from such compositions. The NIR fluorophores can be excited and the ensuing fluorescence can be detected. The detected fluorescence is used to identify and sort polymers and containers. The process is particularly useful for the recycling used containers.

U.S. Pat. No. 5,614,008 provides inks which comprise a water-dissipatable polyester, NIR fluorophores, a humectant, a lower aliphatic alcohol, and water. The inks, which are nearly invisible to the human eye, can be used to mark the surface of articles for identification, authentication, sorting, etc.

U.S. Pat. No. 5,783,307 provides a UV stabilized multi-layer structure which has an easily visible UV protective layer and an underlying polymeric layer. The UV protective layer contains a UV absorber which may be a fluorescent material. It also contains an optical brightener which has fluorescent properties to make the UV protective layer visibly illuminated upon exposure to a UV or a white light source.

U.S. Pat. No. 5,804,447 provides the use of certain compounds as markers for liquids. The compounds are from the class of the phthalocyanines, naphthalocyanines, nickel dithiolene complexes, aminium compounds of aromatic amines, methine dyes or azule-nesquaric acid dyes. The compounds have absorption maximum in the range of 600 to 1200 nm and/or fluorescence maximum in the range of 620 to 1200 nm. The absorption and/or fluorescence wavelengths are detected and used to identify previously marked liquids.

U.S. Pat. No. 4,305,816 provides a method and apparatus for testing open ended containers. The patent mentions aluminum containers and the testing thereof for wall integrity. The patent provides lighting of the container walls using a quartz source. Defects are detected by photodiodes which detect light transmitted through the wall of the container.

SUMMARY OF THE INVENTION

This invention relates to a method comprising the following steps: forming an article comprising a layer comprising a known concentration and a substantially uniform distribution of fluorophores; exposing at least a portion of the layer to electromagnetic radiation to create a fluorescent signal; measuring the fluorescent signal to determine the thickness of the layer.

This invention also relates to a method comprising the following steps: forming an article comprising a layer comprising a known concentration and a substantially uniform distribution of fluorophores; exposing at least a portion of the layer to electromagnetic radiation to create a fluorescent signal; measuring the fluorescent signal to determine non-uniformity in thickness of the layer.

The methods of the present invention may be used to control the thickness of the layer(s) and may be applied to films, preforms, or other articles comprising individual layers or multiple layers.

DETAILED DESCRIPTION OF THE INVENTION

Figure 1:
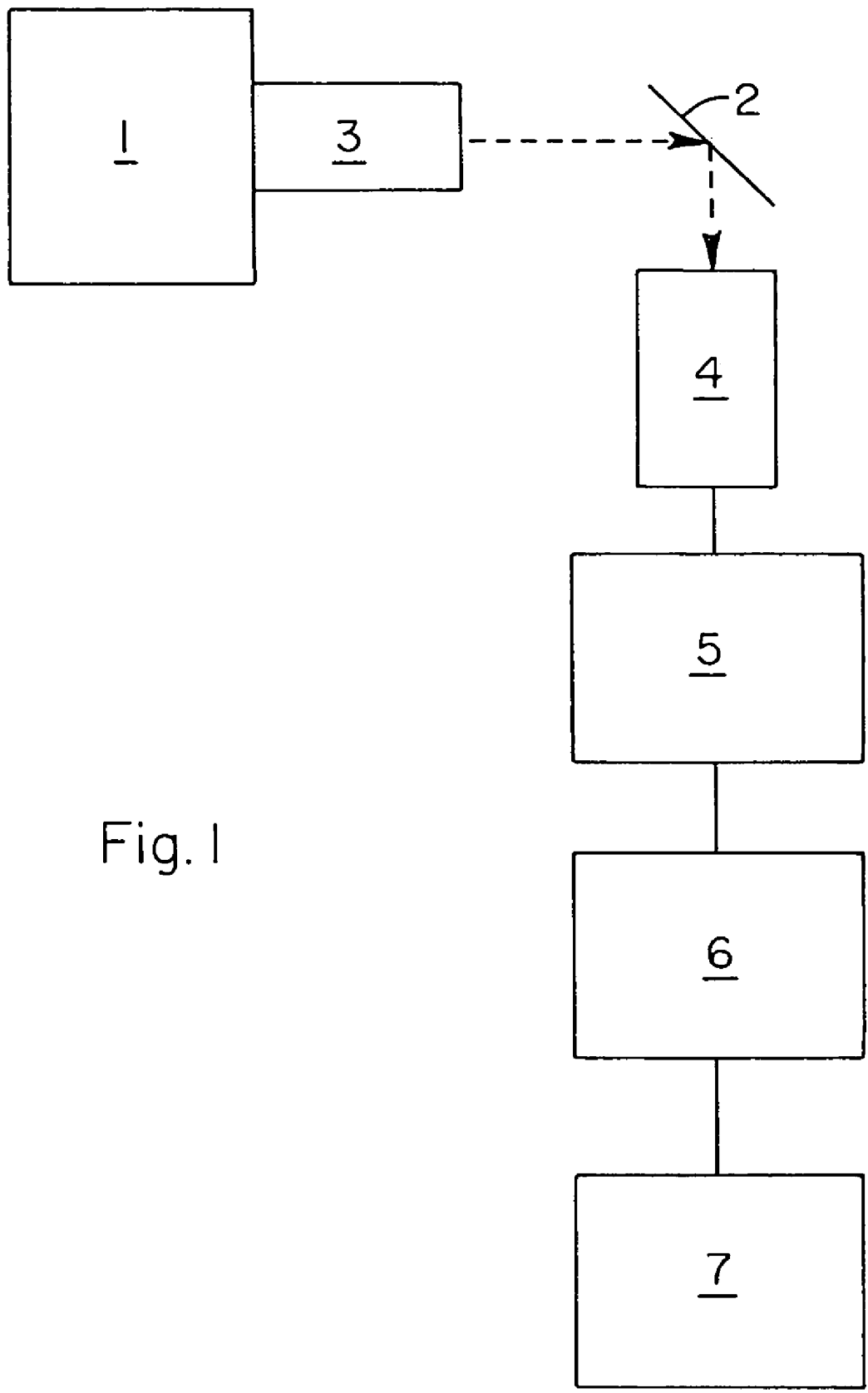
FIG. 1 depicts an apparatus useful for practicing the present invention.

The invention provides an improved method for determining layer thickness, and non-uniformity in layer thickness, using fluorescent compounds.

The invention relates to a method for measuring the thickness of one or more layers of an article. The present invention also relates to a method for measuring the presence of non-uniformity in thickness of one or more layers.

An even further aspect of the invention relates to a method of measuring the thickness of one or more layers of items other than films or preforms—such as layers of a liquid, or mixture of a liquid and a solid. Suitable liquid or liquid/solid layers include, but are not limited to coatings.

The present invention further relates to a method for controlling the thickness of one or more layers of an article. Each of the one or more layers comprises a known concentration and a substantially uniform distribution of fluorophores. The fluorophores may absorb and fluoresce at near infrared (NIR), ultraviolet (UV), or visible wavelengths. They are added to the one or more layers in sufficient quantity to impart fluorescence capable of detection by a detector when exposed to electromagnetic radiation at absorbing wavelengths. Because each of the one or more layers contains a known concentration and a substantially uniform distribution of the fluorophores, the detected fluorescent signal is a predictable function of the thickness of each of the one or more layers. Hence, the thickness and uniformity of each of the one or more layers can be determined and controlled. It should be appreciated that the thickness can be controlled to a standard uniform thickness, or to a varying thickness across the article.

In the above methods of the invention, it will be appreciated that fluorophore compounds are located within the one or more layers for the purpose of determining either the thickness or non-uniformity in thickness of the one or more layers. The fluorophore compounds can be mixed, admixed, blended, copolymerized, or otherwise combined with the layers.

In the methods of the invention, it will be appreciated that radiation detection means or detectors denotes any apparatus capable of detecting fluorescence in the ranges described herein. Such detectors are the devices for detecting photons emitted by the fluorophore compounds at wavelengths in the NIR, UV, or visible range such as photomultiplier tubes, solid state detectors, semiconductor based detectors, imaging devices, or other such devices. The preferred means of detection has an optimum sensitivity at the wavelength region of fluorescence. Examples include but are not limited to silicon photodiodes, germanium detectors, and the like.

The term near infrared (NIR) generally refers to wavelengths in the range of about 670 nm to about 2500 nm. The term ultraviolet (UV) generally refers to wavelengths in the range of about 315 to about 400 nm. The term visible generally refers to wavelengths in the range of about 400 to about 700 nm. However the edges of these ranges are not critical to the invention; for example, the upper bound of the NIR range could extend above about 2500 nm, and the lower bound of the UV range could extend below about 315 nm.

The term "light sources" refers to devices, used to irradiate the fluorophores with NIR, visible, or UV radiation, such as laser diodes, solid state lasers, dye lasers, incandescent, or any other known light source. Such light sources can be used in conjunction with wavelength selectors such as filters, monochromators, etc. The preferred light sources are those that have a maximum signal at or near the maximum of the absorbance of the fluorophore compounds. Examples include laser diodes, light emitting diodes, or solid state lasers.

The term "article" refers to sheet, film, tubing, profiles, preforms, fiber, woven and shaped articles, such as containers, thermoformed articles such as trays, and the like. Generally, the term "film" refers to thin structures comprising one or more layers. The film may comprise polymeric material, non-polymeric material, or combinations thereof, and may be of virtually any thickness. However, the thickness is generally substantially less than either of the two dimensions orthogonal to the thickness. The term "film" is intended to include structures commonly used in the art generally described as films, sheets, layers, laminates, or coatings, and other similar structures. The term "film" is also intended to include the relatively thin walls of plastic containers commonly used in the art to contain beverages such as soda, beer, or juice.

The term "preform" refers to tubular structures closed at one end, which can be molded into bottles or other generally cylindrical containers. Preforms are typically blow molded into such bottles or other cylindrical containers. The open end is typically called the neck region, and is the region to which blow molding equipment generally will attach. The closed end is typically called the base region. The material between the neck region and the base region is often called the body. A preform comprises polymeric material or combinations of polymeric and nonpolymeric material. The preform may have one or more layers. The number of layers may vary with respect to axial position along the tubular axis of the preform. For example, the number of layers within the neck region, the base region, and the remaining body of the preform may be different. The term "preform" is intended to include structures commonly used in the art generally described as preforms, parisons, and other similar structures.

In the method of the invention, the phrase "detectibly different wavelengths" refers to the phenomenon that fluorescence by fluorophore compounds having different compositions may occur at a different wavelengths and such difference will, by necessity be one that is capable of detection. Using state of the art detection equipment it is believed that such differences in absorption/fluorescence of as little as 20 nm in wavelength can be discerned. Of course, this limitation is not critical and will decrease as detection methodology improves.

The presence of NIR UV, or visible fluorophores provides an effective method for determining the thickness or non-uniformity of thickness of a layer of a polymer film or preform. Although it is preferred that the fluorophores absorb and fluoresce at wavelengths at which the polymers are generally transparent, use of such fluorophores is not necessary. As will be described later, the predictable function between fluorescent signal and layer thickness is calibratible. Should the polymer itself absorb within the wavelength range at which a fluorophore absorbs or fluoresces, the polymer's absorbtion can be accommodated by the calibratible nature of the predictable function. It is recognized that many polymers themselves absorb UV radiation, and that such polymers will involve this polymer absorbtion effect.

Ideally, for the practice of certain aspects of this invention, the fluorophore compounds should have excellent thermal stability and little light absorption in the visible region at the concentrations they are used; that is, they should impart little or no color to the layer with which the fluorophores are mixed, copolymerized, or otherwise combined. Also within these aspects of the invention, they should have strong absorption of NIR or UV radiation (high molar extinction coefficients, e.g. >about 20,000) and have strong fluorescence in the NIR or UV wavelengths. Suitable stability to sunlight and fluorescent light and low extractability or sublimation from the thermoplastic compositions are also preferred. To appear essentially invisible to the eye the layers containing the fluorophores should absorb little light in the visible range which extends from about 400 nm to about 700 nm. However, because of the low concentration of the fluorophore compound used in the layers, even fluorophores which would impart color at high concentrations may be used in the present invention, so long as the concentration at which the fluorophores is used is insufficient to impart discernable color.

In aspects of the invention in which it is acceptable to impart color to the layer, the restrictions of the previous paragraph are reduced. Hence, in the practice of such aspects of the invention, fluorophore compounds which have substantial visible absorbance or fluorescence may be used.

Suitable NIR fluorophore compounds for the invention include, but are not limited to, those described in U.S. Pat. Nos. 5,703,229; 5,553,714; 5,461,136; and 5,397,819, which are incorporated herein by reference. Suitable compounds include, but are not limited to, those selected from the classes of phthalocyanines, naphthalocyanines, squaraines (derivatives of squaric acid), carbocyanines, and zethrens, such as quatterylenes. The compounds may contain one or more metals, such as aluminum, or may be metal free. Non-limiting specific examples include 2(3), 9(10), 16(17), 23(24)-tetraphenoxy-Pc—Al—[O—(3,5-dimethoxycarbonyl)phen-1-yl)] (Pc refers to a phthalocyanine moiety); 2(3), 9(10), 16(17), 23(24)-tetra-(4-t-butyl-1-phenylthio)-PcAl—[O—(3, 5-dimethoxycarbonyl)phen-1-yl]; 2(3), 9(10), 16(17), 23(24)-tetra-(SC$_6$H$_5$)-PcAl—[O—(3,5-dimethoxyarbonyl)phen-1-yl]; 1(4), 8(11), 15(18), 22(25)-tetra-(SC$_6$H$_5$)-PcAl—[O—(3,5-dimethoxycarbonyl)phen-1]; 1(4), 8(11), 15(18), 22(25)-tetra-(SC$_6$H$_5$)-PcAl—[O—(3,5-dimethoxycarbonyl)phen-1-yl]; 1, 2, 3, 4, 8, 9, 10, 11, 15, 16, 17, 18, 22, 23, 24, 25-hexadeca (SC$_6$H$_5$)-PcAl[O—3,5-dimethoxycarbonyl)phen-1-yl]; 2, 3, 9, 10, 16, 17, 23, 24-octa-(SC$_6$H$_5$)-PcAl[O—(3, 5-dimethoxycarbonyyl)phen-1-yl]; 2(3), 9(10), 16(17), 23(24) tetraphenoxy-PcSi—(OC$_6$H$_4$-4-CO$_2$CH$_3$)$_2$; 5(36), 9(14), 18(23), 27(32) tetraphenyl-NcAlCl (Nc refers to a naphthalocyanine moiety); 2(3), 11(12), 20(21), 29(30)-tetra-t-butyl-NcAlCl; 2(3), 11(12), 20(21), 29(30)-tetra-t-butyl-NcAlOH; aluminum phthalocyanine chloride; aluminum phthalocyanine (3,5-dicarbomethoxyphenoxide); 1(4),8(11),15(18),22(25)-tetrakis((4-(2-ethylhexoxy)carbonyl)phenoxy)phthalocyanine; 1,1,3,3,3,3,-hexamethyl-4,4,5,5-dibenzo-2,2-indotricarbocyanine perchlorate; 5,5-dichloro-11-(diphenylamino)-3,3-diethyl-10,12-ethylethiatricarbocyanine perchlorate; 2-[2-[2-(diphenylamino)-3-[[3-(4-methoxy-4-oxybutyl)naphtho[2,3-d]thiazol-2(3H)-ylidene]ethylidene]-1cyclopenten-1-yl]ethyenyl]-3-(4-methoxy-4-oxobutyl)-naphtho[2,3-d]thiazolium perchlorate; 4,5-benzoindotricabocyanine; and other similar compounds, including those not specifically mentioned in this paragraph but described in U.S. Pat. Nos. 5,703,229; 5,553,714; 5,461,136; and 5,397,819.

Suitable fluorophore compounds useful for the invention which absorb/fluoresce in the UV and/or visible ranges can be selected, for example, from the following classes of compounds: 1,2-diarylethenes; 2-arylbenzazoles; 2(H)-1-benzopyran-2-ones (also known as coumarins); 2(H)-1-benzopyrane-2-imines (also known as imonocoumarins); carbostyrils; 3(H)-1-naphtho[2,1-b]pyran-ones; 3(H)naphtho[2,1-b]pyran-3-imines; aminophthalimides; 1,8-naphthalenedicarboximides; 1,4,5,8-naphthalenetetracarboxyli acid diimides; 2,5-diarylthiophenes; 2,5-diarylfurans; 2,5-diaryl-1,3,4-thiadiazoles, 2-arylnbenzofurans; 2,6-diphenylbenzodifurans; 2,2-bis(5-phenyl-1,3,4-oxadiazoles); quinolines; quinoxalines; 3,4-diarylfuranones; distyrylarenes; 7(H)benzananthracence-7-ones (also known as benzanthrones); polyarenes; and the like. Non-limiting examples of specific compounds useful for the invention are listed as Fluorescent Brighteners in the Colour Index published by The Society of Dyers and Colourists in association with the American Association of Textile Chemists and Colorists. Specific Fluorescent Brighteners useful for the invention include, but are not limited to, Colour Index Fluorescent Brightener 1, Colour Index Fluorescent Brightener 24, Colour Index Fluorescent Brightener 28, Fluorescent Brightener 68, Colour Index Fluorescent Brightener 86, Colour Index Fluorescent Brightener 134, Colour Index Fluorescent Brightener 135, Colour Index Fluorescent Brightener 175, Colour Index Fluorescent Brightener 185, Colour Index Fluorescent Brightener 208, Colour Index Fluorescent Brightener 210 and Colour Index Fluorescent Brightener 252, titanium dioxide, and the compound represented by the following formula.

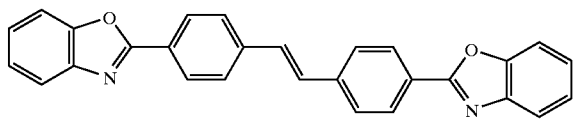

Other non-limiting examples of fluorescent compounds that can be reacted into polymers through an ester or hydroxyl functionality include dimethyl 2,6-naphthalenedicarboxylate and the following compounds described within U.S. Pat. No. 4,892,923 (Example 1); U.S. Pat. No. 4,882,412 (Example, structure shown below) U.S. Pat. No. 4,803,241 (Example 2); U.S. Pat. No. 3,709,896 (Example 1); and U.S. Pat. No. 5,091,501 (Example 6), which are incorporated herein by reference:

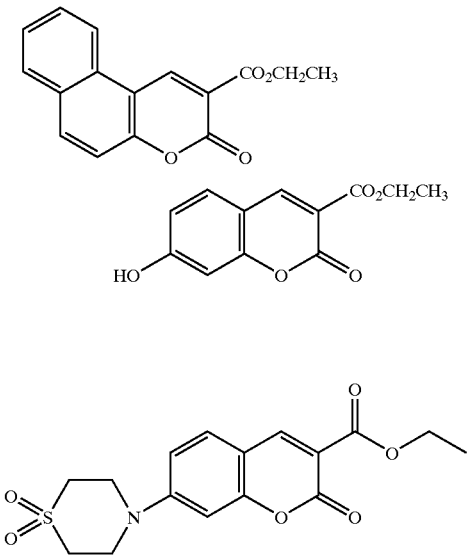

Further examples of fluorophore compounds useful for the invention which absorb/fluoresce in the UV and/or visible ranges and which can be admixed into polymers can be selected, for example, from classes of compounds such as naphthalimides, aminoketones, lactones, coumarins, thixanthone benzanthrones, anthrapyridones, benzopyrans, thioindigoids, anthraquinones, perylenes, stilbenes, and the like. Specific examples useful for the invention include, but are not limited to, 7-(diethylamino)-2-oxo-2H-1-benzopyran-3-carbonitrile, Colour Index Solvent Yellow 44, Colour Index Solvent Yellow 98, Colour Index Solvent Yellow 131, Colour Index Solvent Yellow 135, Colour Index Solvent Yellow 160:1, Colour Index Solvent Yellow 185, Colour Index Solvent Orange 63, Colour Index Solvent Red 149, Colour Index Solvent Red 197, Colour Index Solvent Red 197, Colour Index Solvent Red 242, Colour Index Solvent Blue 59 and Colour Index Solvent Green 5.

Other examples of fluorophore compounds useful for the invention which absorb/fluoresce in the UV and/or visible ranges and which can be copolymerized include the following compounds described within U.S. Pat. No. 5,091,501 (Example 8), U.S. Pat. No. 5,274,072 (Example 21, yellow), U.S. Pat. No. 5,030,708 (Example 8, bluish red), U.S. Pat. Nos. 5,106,942 (5,106,942), and 4,892,922 (Example I, yellow), which are incorporated herein by reference.

The choice of fluorophore compound or fluorophore compounds is not critical. Virtually any fluorophore compound can be used if the compound can be effectively mixed, co-polymerized, or otherwise combined with the layer, and if the fluorophore compound satisfies other restrictions described herein.

The layers containing fluorophore compounds may be combined with other layers to form a multi-layer film or preform. Such a multi-layer film or preform may contain one or more layers with fluorophore compounds, and one or more layers without fluorophore compounds. Each layer containing a fluorophore compound may contain one or more fluorophore compounds, and should contain fluorophore compounds which fluoresce at a detectibly different wavelength or wavelengths than the fluorophore compounds in other layers having fluorophore compounds.

The various layers, both with or without fluorophore compounds, comprise polymeric materials, non-polymeric materials, or combinations thereof. The materials should be chosen such that a film or preform containing fluorophore compounds is clear or translucent at the incident and emitted light wavelengths, so that the incident and emitted light is readily transmitted through the film or preform. However, a backing layer which does not contain fluorophore compounds may be opaque. Suitable materials include a wide variety of polymers, such as polyesters, polyolefins, vinyl polymers, polycarbonates, polyurethanes, polysulfones, polyethers, polyacetals, polyacrylates, polyamides, polyepoxies, other similar polymers, copolymers, and blends thereof. Useful non-polymeric materials include non-polymeric waxes. Useful non-polymeric materials also include glass fibers or other reinforcing materials, various antiblocking materials, slip agents, or various other additives. In addition, particularly for backing layers, useful non-polymeric materials also include various glasses and other materials useful for such layers.

Useful types of polyesters of this invention include linear, thermoplastic, crystalline or amorphous. Particularly useful polyesters include poly(ethylene terephthalate) and poly(butylene terephthalate). The polyesters can be produced using typical polycondensation techniques well known in the art.

The diol components of the polyester may be comprised of, for example: ethylene glycol; propanediol; butanediol; pentanediol; neopentyldiol; hexanediol; decanediol; 1,4-cyclohexanedimethanol; 1,2-propanediol; 1,3-propanediol; 2-methyl-1,3-propanediol; 3-methyl-2,4-pentanediol; 2-methyl-1,4-pentanediol; 2,2,4-trimethylpentane-1,3-diol; 2-ethyl-1,3-hexanediol; 2,2-diethyl-1,3-propanediol; 1,4-di(hydroxyethoxy)-benzene; 1,6-hexanediol; 1,2-cyclohexanediol; 1,4-cyclohexanediol; 1,10-decanediol; 1,2-cyclohexanedimethanol; 1,3-cyclohexanedimethanol; 1,4-cyclohexanedimethanol; X,8-bis-(hydroxymethyl)-tricyclo-[5.2.1.0]-decane wherein X represents 3, 4, or 5; diols containing one or more oxygen atoms in the chain, e.g., diethylene glycol, triethylene glycol, dipropylene glycol, tripropylene glycol, poly(ethylene glycol), poly(propylene glycol), or poly(tetramethylene glycol); derivatives thereof; and the like. In general, these diols contain 2 to 18, preferably 2 to 12 carbon atoms. Cycloaliphatic diols can be employed in their cis or trans configuration or as a mixture of both forms. Aliphatic diols can be employed in their various isomeric forms or as a mixture of such forms.

The acid components (aliphatic, alicyclic, or aromatic dicarboxylic acids) of the polyester may be comprised of, for example, terephthalic acid, phthalic acid, isophthalic acid, naphthalene-2,6-dicarboxylic acid, 1,4-cyclohexanedicarboxylic acid, 1,3-cyclohexanedicarboxylic acid, succinic acid, glutaric acid, adipic acid, suberic acid, azelaic acid, sebacic acid, sulfoisophthalic acid, hydroxybenzoic acid, 1,12-dodecanedioic acid, cyclodiacetic acid, diphenyl-4,4'-dicarboxylic acid, derivatives thereof, various isomers, and the like. In place of the dicarboxylic acids themselves, it is possible and often preferable to use a functional acid derivative thereof such as the dimethyl, diethyl, or dipropyl ester of the dicarboxylic acid. Other esters such as various sulfoisophthalates, e.g. sodium sulfoisophthalate, could also be used. The anhydrides of the dicarboxylic acids can likewise be employed.

The polyesters may also comprise small amounts of trifunctional, tetrafunctional, or other multifunctional comonomers such as trimellitic anhydride; trimethylolpropane; pyromellitic dianhydride; pentaerythritol; and other polyester forming multifunctional comonomers generally known in the art.

Typical polycarbonates useful in the practice of the invention are disclosed in Kirk-Othmer Encyclopedia of Chemical Technology, third edition, Vol. 18, pp 479–494.

Suitable polyamides include partially aromatic polyamides, aliphatic polyamides, wholly aromatic polyamides and mixtures and copolymers thereof. By "partially aromatic polyamide" it is meant that the amide linkage of the partially aromatic polyamide contains at least one aromatic ring and a nonaromatic species.

Suitable polyamides have a film forming molecular weight and preferably an I.V. of about 0.25 to about 1.5 dL/g, preferably about 0.4 to about 1.2 dL/g, and more preferably of about 0.7 to about 0.9 dL/g. The I.V. is measured at 25° C. in a 60/40 by weight mixture in phenol/1,1,2,2-tetrachloroethane at a concentration of 0.5 grams per 100 ml. Wholly aromatic polyamides comprise in the molecule chain at least 70 mole % of structural units derived from m-xylylene diamine or a xylylene diamine mixture comprising m-xylylene diamine and up to 30% of p-xylylene diamine and an αε-aliphatic dicarboxylic acid having 6 to 10 carbon atoms, which are further described in Japanese Patent Publications No. 1156/75, No. 5751/75, No. 5735/75 and No. 10196/75 and Japanese Patent Application Laid-Open Specification No. 29697/75, the disclosure of which is incorporated herein by reference.

Polyamides formed from isophthalic acid, terephthalic acid, cyclohexanedicarboxylic acid, meta- or para-xylylene diamine, 1,3- or 1,4-cyclohexane(bis)methylamine, aliphatic diacids with 6 to 12 carbon atoms, aliphatic amino acids or lactams with 6 to 12 carbon atoms, aliphatic diamines with 4 to 12 carbon atoms, and other generally known polyamide forming diacids and diamines can be used. The low molecular weight polyamides may also contain small amounts of trifunctional or tetrafunctional comonomers such as trimellitic anhydride, pyromellitic dianhydride, or other polyamide forming polyacids and polyamines known in the art.

Preferred partially aromatic polyamides include: poly(m-xylylene adipamide), poly(m-xylylene adipamide-co-isophthalamide), poly(hexamethylene isophthalamide), poly(hexamethylene isophthalamide-co-terephthalamide), poly (hexamethylene adipamide-co-isophthalamide), poly (hexamethylene adipamide-co-terephthalamide), poly (hexamethylene isophthalamide-co-terephthalamide) and the like or mixtures thereof. More preferred partially aromatic polyamides include, but are not limited to poly(m-xylylene adipamide), poly(hexamethylene isophthalamide-co-terephthalamide), poly(m-xylylene adipamide-co-isophthalamide), and mixtures thereof. The most preferred partially aromatic polyamide is poly(m-xylylene adipamide), which is available from Mitsubishi Gas and Chemical Company, Chiyodaku, Tokyo, Japan. Poly(m-xylylene adipamide) is a preferred polyamide due to its availability, high gas barrier properties, and processability in conjunction with PET.

Suitable aliphatic polyamides include polycapramide (nylon 6), poly-aminoheptanoic acid (nylon 7), poly-aminononanoic acid (nylon 9), polyundecane-amide (nylon 11), polyaurylactam (nylon 12), polyethyleneadipamide (nylon 2,6), polytetramethylene-adipamide (nylon 4,6), polyhexamethylene-adipamide (nylon 6,6), polyhexamethylene-sebacamide (nylon 6,10), polyhexamethylene-dodecamide (nylon 6,12), polyoctamethylene-adipamide (nylon 8,6), polydecamethylene-adipamide (nylon 10,6), polydodecamethyleneadipamide (nylon 12,6) and polydodecamethylene-sebacamide (nylon 12,8).

Preferred aliphatic polyamides include poly(hexamethylene adipamide) and poly(caprolactam). The most preferred aliphatic polyamide is poly(hexamethylene adipamide). Partially aromatic polyamides, are preferred over the aliphatic polyamides where good thermal properties are crucial.

The most preferred polyamides include poly(m -xylylene adipamide), polycapramide (nylon 6), polyhexamethyleneadipamide (nylon 6,6).

The polyamides are generally prepared by processes which are well known in the art.

Co-curable compounds of polyepoxides and polyamines may also be used. Examples include the reaction product of a polyepoxide and an ungelled amine-functional polymeric resin which comprises the reaction product of: (i) a polyamine characterized as having up to about two primary amino nitrogen groups per molecule; and (ii) a polyepoxide, a polyoxalate or a polyacrylate. Generally, the ratio of the ungelled amine-functional resin to polyepoxide is from about 0.1:1 to about 1:1, preferably from about 0.2:1 to about 0.8:1 based upon epoxy groups to amine hydrogens.

A wide variety of polyepoxides may be utilized in forming the ungelled amine-functional polyamine resin. The polyepoxides may be saturated or unsaturated, aliphatic, cycloaliphatic, aromatic, or heterocyclic and may be substituted, if desired, with noninterferring substituents such as hydroxyl groups or the like.

Examples of useful polyepoxides are polyglycidyl ethers of aromatic polyols, e.g., polyphenols. Such polyepoxides can be produced, for example, by etherification of an aromatic polyol with epichlorohydrin or dichlorohydrin in the presence of an alkali. Additional specific examples of suitable polyepoxide/polyamine reaction products are known and may be found in U.S. Pat. Nos. 5,491,204; 5,902,643; 5,637,365; 5,840,825; 5,728,439; 5,652,034 and 5,498,455, the disclosures of which are incorporated herein by reference. Polymers of this type are available from PPG Industries, Inc. under the tradename, Bairocode.

Other thermoplastic polymers suitable for the invention would include a wide range of such polymers known in the art, such as, but not limited to, polyolefins, e.g., polypropylene, polyethylene, linear low density polyethylene, polybutylene and copolymers made from ethylene, propylene and/or butylene; vinyl polymers, e.g., polyvinyl chloride and polyvinylidene chloride; cellulose esters, e.g., cellulose acetate, propionate, butyrate or mixed esters; polyurethanes; polysulfones; polyacetals, polyacrylates, e.g., poly(methyl methacrylate); polyimides; polyester-amides; polystyrenes; polyethers; ABS (acrylonitrile-butadiene-styrene) type polymers, (TPO) thermoplastic oligomers, other similar polymers, and copolymers thereof.

The polymeric materials, non-polymeric materials, and combinations thereof may be used individually to make layers of a film. In addition, the polymeric materials and combinations of polymeric materials and non-polymeric materials may be used to make layers of a preform. The materials may be mixed, blended, copolymerized, or otherwise combined to make particular layers. Fluorophore compounds may be included with the compositions of any or all of the layers according to the desire to measure thickness or non-uniformity in thickness of a particular layer. It is recognized that the optical paths at the irradiating and fluorescing wavelengths must be sufficiently clear to transmit a sufficient amount of irradiating and fluorescent electromagnetic waves.

The fluorophore compounds may be incorporated into the materials of the various layers using conventional techniques. For example, fluorophore compounds may be incorporated into thermoplastic resins using conventional techniques such as those employed to incorporate other additives in such resins (see R. Gachter and H. Mueller, Editors, Plastics Additives Handbook, Hansu Publishers, New York, 1985, pp 507–533; 729–741). For example, fluorophore compounds may be dry blended in the form of powders with thermoplastic materials in the form of pellets or powders, with or without an adhesion promoter or a dispersing agent. This premix can be subsequently processed on extruders or molding machines. In some cases, solution blending may also be preferable. In addition to the above, the fluorophore compounds may be copolymerized with the thermoplastic resins. Of course, other conventional additives such as plasticizers, antioxidants, stabilizers, nucleating agents, etc., may also be present in the thermoplastic compositions of the invention.

The levels of the fluorophore compounds present in the final thermoplastic composition may vary considerably depending upon the molar extinction coefficient and the fluorescing efficiency (i.e., fluorescent quantum yield) of the added fluorophore in the polymer matrix. It is generally desirable that the fluorophore be present at the lowest practical level needed to produce a satisfactory fluorescence detection level to minimize any color problems resulting from the presence of the fluorophore in the thermoplastic and to minimize cost. Normally, with suitable fluorescence efficiency the fluorophore compounds are added in the amount of from about 0.5 ppm to about 100 ppm, with about 1 ppm to about 10 ppm being preferred. However it should be recognized that the amount of the fluorophore—within the considerations described herein—is not critical.

The resultant film can be made by techniques well known in the art. Typically, a thermoplastic composition is prepared for each layer. The compositions are typically co-extruded (extruded in the case of a single layer) into the desired film. The resultant films will generally have a thickness of about 0.5 mil to about 250 mils (0.0125 mm to about 6 mm). Although the thickness of the layer or layers containing the fluorophores is not critical, they will generally have a thickness of about 0.1 mil to about 10 mils (0.0025 mm to about 0.25 mm). The films will typically contain one, two, three, or more layers.

In addition to extrusion and co-extrusion, the films can be made using virtually any manufacturing process known to the art. Examples of other processes include injection blow molding, co-injection blow molding, extrusion blow molding, co-extrusion blow molding, stretch blow molding, solution coating, spin blowing, lamination processes, injection molding, co-injection molding, and other processes commonly known in the art.

The resultant preform can be made by techniques well known in the art. Typically a thermoplastic composition is prepared for each layer. The compositions are typically co-extruded (extruded in the case of a single layer) or co-injection molded (injection molded in the case of a single layer) into the desired preform. The resultant preforms will generally have a body with a thickness of about 50 mils to about 500 mils (1.25 mm to about 12.5 mm). Although the thickness of the layer or layers containing the fluorophores is not critical, they will generally have a thickness of about 0.5 mil to about 300 mils (0.0125 mm to about 7.5 mm). Alternatively, the thickness of a single layer can be about 1% to about 60% of the thickness of the preform body itself. The preforms will typically contain one, two, three, or more layers.

The resultant application for the film or preform is not critical. For example the invention can be used to measure the thickness or non-uniformity of thickness of preforms used to make containers for beverages such as, but not limited to soda, beer, or juice. Other Suitable applications for the articles include films used for wrappers for packaging; various displays; signs; and containers for beverages. Other illustrative applications include films created by solution coating processes in the photographic industry, coatings for adhesive applications, floor coatings, and hardcoats.

Frequently films of the present invention will be used to improve at least one property of the article to which they are applied or incorporated. For example, in food packaging the films which provide improved barrier to gasses such as oxygen and carbon dioxide are needed. The films can provide passive barrier (increased impermeability), active barrier (the film actually removes undesired compounds from the contents, such as oxygen scavenging) or a combination of both. Passive barrier can be provided by selecting appropriate polymeric materials, such as certain polyamides, polyesters having high naphthalene dicarboxylate or isophthalate modification or content, polyamine/polyepoxide reaction products and the like. The barrier of these materials can be further enhanced through incorporation of other barrier enhancing compounds, such as well dispersed platelet particles derived from certain clay materials. Suitable platelet particles are known in the art and disclosed in US99/28981 and US99/28220, the disclosure of which is incorporated by reference. Active barrier compounds, such as oxygen scavenging compounds as also well known, and include a variety of compounds capable of reacting with oxygen and, preferably, a transition metal catalyst. These materials are expensive and can add considerable cost to the final article. Thus, the present invention provides a simple and effective process for controlling the amount of performance materials incorporated into an article.

Preforms can be made into containers by any method commonly used in the art. Typical methods include extrusion blow molding, injection blow molding, and stretch blow molding. For extrusion blow molding, materials are extruded or co-extruded to make a preform, and the preform is blow molded into the final shape of the container. For injection blow molding, materials are injection or co-injection molded to make a preform, and the molten preform is transferred from the core rod to the blow station. The molten preform is blow molded into its final shape at the blow station. For stretch blow molding, a preform is formed by an injection or coinjection molding process. The preform is then reheated with infrared heaters in a secondary process and blow molded into the final shape of the container. For all processes, the preform may comprise one or more layers. The resultant container will comprise one or more layers, reflecting the layer structure of the preform.

Another technique that can be used to make a container is the process of overmolding where molten material is injection molded over a core pin. Lamination processes commonly known to those skilled in the art can be used to add additional layers to create a multilayer bottle.

The thickness or non-uniformity of thickness measurements can be made off-line after manufacture of the film or preform. For example, they can be used off-line to inspect the film or preform as part of quality control. For example, the measurements can be used to ensure that the film or preform thickness is within the intended range of thickness. Alternatively, the measurements can be made on-line during the manufacture of the film or preform. For example, they can be made on-line as an active system control during the manufacturing process. The thicknesses or non-uniformities of thickness of multiple layers can be simultaneously determined and controlled by monitoring the fluorescence of the fluorophore compounds (each with a different emission spectra) in each of the multiple layers and using the information to control the molding process.

The invention can be used on-line in determining the thickness or non-uniformity of thickness of extruded or coextruded layers during the extrusion or coextrusion process for cast or blown film. In addition, the invention can be used on-line in determining the thickness or non-uniformity of thickness of injected or co-injected layers during the injection or co-injection molding process. An example is the measurement of the thickness or non-uniformity of thickness of a barrier layer in a preform for a beverage container—particularly a thermoplastic container used for beer, soda, or other carbonated beverage. The thickness and non-uniformity of thickness of the barrier layer is particularly important, because a thin section in the barrier layer could substantially degrade the performance of the resultant container. In addition, on-line measurements could also be used for other forms of quality control.

It should be recognized that the measurements can be made over any chosen section of the film or preform. In addition, the measurements may be made in combination with other measurements, such as other measurements commonly made for quality control.

In the making of actual measurements, the fluorophores are irradiated with light of known frequency and magnitude content from the light sources of the types described earlier. The resultant fluorescence is detected with detection means of the types described earlier. The detected fluorescence is a predictable function of the thickness of each of the one or more layers. Using this predictable function, the fluorescence is converted into a measurement of the thickness or non-uniformity of thickness.

The predictable function relating fluorescence and thickness is calculated by recognizing that the layer contains a known concentration and a substantially uniform distribution of the fluorophores. Hence, the number of fluorophores per unit thickness for a given layer area is known. Since the magnitude of the fluorescent signal, in each frequency range of fluorescence, is a known or calibratible function of the number of fluorescing fluorophores, the magnitude of the fluorescing signal over the given area, in one or more of the frequency ranges, will enable calculation of the thickness. It is recognized that the known calibratible function may be linear or non-linear.

An apparatus useful for practicing the present invention for measuring the thickness of one or more polymer layers (or for determining non-uniformities in thickness of one or more polymer layers) is shown in FIG. 1 wherein like numerals reference like parts. This arrangement will be understood to be an application of commercially available fluorometers for example manufactured by SLM Aminco of Urbana, Ill. This arrangement is for performing the tests of the present invention for one sample layered structure at a time. As may be seen from FIG. 1, there is present a light source (1) capable of emitting radiation in the range of about 670 to about 2500 nm which illuminates a layer sample (2) through a wavelength selector (3) e.g., monochromator or interference filter. A wavelength selector (4) and a near infrared (NIR) sensitive photodetector (5) is placed at 90 degrees or less angle. The light source (1), wavelength selectors (3 & 4) and photodetector (5) are all arranged on two sides of a triangle to minimize scattered light entering the photodetector (5). The light source (1) in FIG. 1 may be replaced with lasers, preferably semiconductor lasers. The output of photodetector (5) is provided to level adjustment amplifier (6), the output of which is provided to an integrated circuit digital multimeter (7). In a preferred embodiment, digital multimeter (7) is embodied by a computerized unit manufactured by SLM Aminco of Urbana, Ill. The output of the digital multimeter (7) is connected to a computer display (not shown) so as to provide a numeral and graphical indication of the amount of luminous flux at the predetermined wavelength (preferably at or near the emission maxima) emitted by fluorophores contained in the layer sample (2). The level adjustment amplifier (6) should be adjusted to provide an output appropriately scaled to suit digital multimeter (7). The reading from digital multimeter (7) is converted to the layer thickness using the previously described predictable relationship between thickness and fluorescent signal.

Figure 2:
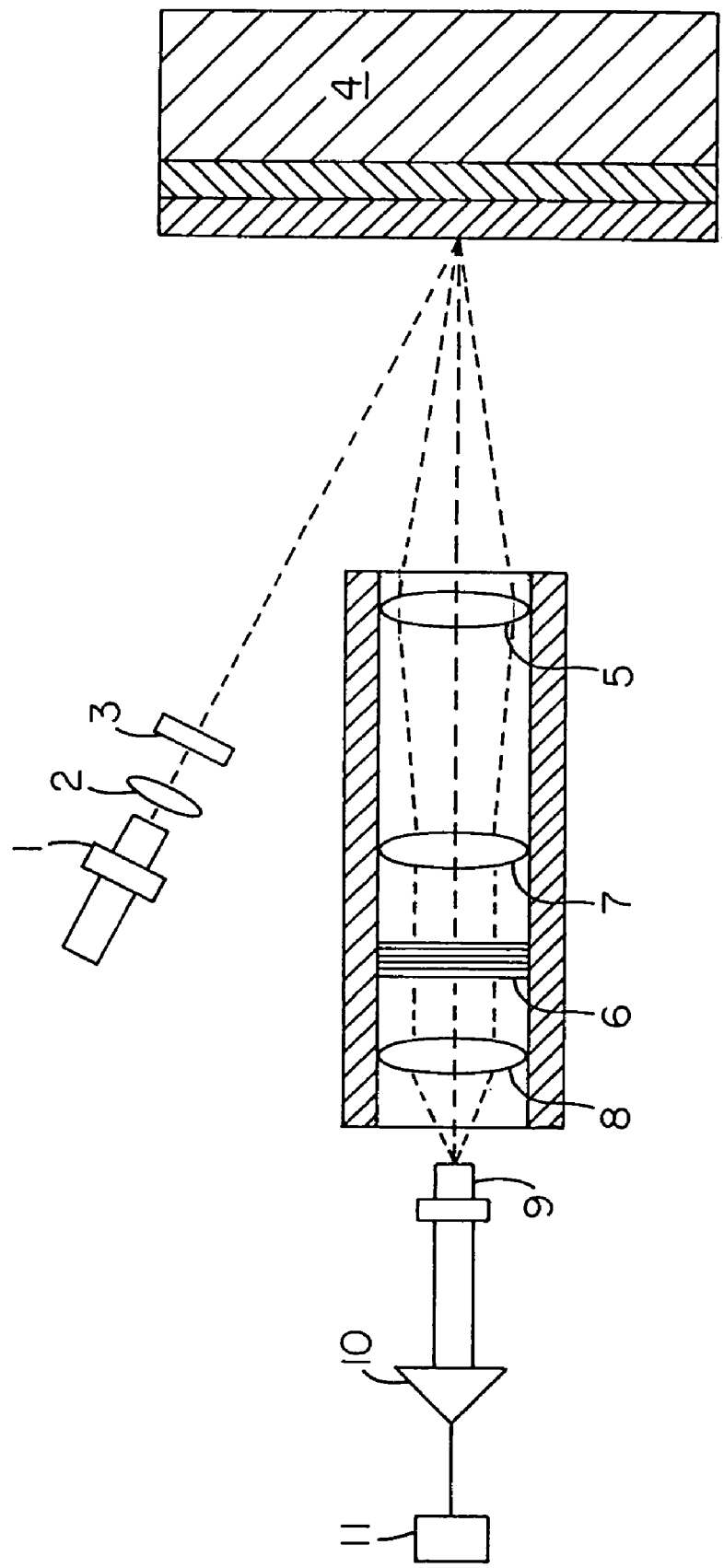
FIG. 2 depicts an apparatus which is a specialized arrangement for performing tests of the present invention.

FIG. 2 shows a preferred apparatus useful for performing the method of the present invention. As may be seen from FIG. 2, there is present a laser diode light source (1) capable of emitting NIR radiation in the range of about 670–2500 nm which is collimated through a collimating lens (2), and illuminates a target layer or layers (4) through an optical filter (3). A focusing lens (5) and a beam compressor are placed at 30 degrees or less angle. The laser diode light source and the collimating lens are arranged to minimize scattered light from entering the detector. An optical filter (6) is placed between the collimating lenses (7 & 8) to select the wavelengths of fluorescence of the NIR fluorophores which is focused on the photodetector (9). A current-to-voltage converter (10) is connected to the photodetector (9) to convert and amplify the detector signal. The arrangement and the electronic circuitry of the current-to-voltage converter (10) is widely known and the routines of amplifying and processing the photodetector signal are also well-known. The signal from the current-to-voltage converter circuit is detected by a detector (11). The reading from the detector is converted into a measurement of the thickness of the one or more layers.

When determining the thickness of multiple fluorophore compounds (such as for the measurement of the thickness of multiple layers), the use of multiple apparatus as shown in FIG. 2 may be necessary. If more than one unit are used, the optical path (i.e., the optical axis) of the light sources and/or detectors may partially or totally overlap to illuminate the same spot. The choice of fluorophore compounds is dependent on their spectral properties, wherein the absorption and fluorescence maxima are sufficiently separated that they have detectibly different wavelengths to allow for identification of individual layer thicknesses (e.g., about 20 nm or more). The multiplexing and computing apparatus required is within the ability of one of ordinary skill in the art.

In addition, for the use of the invention on-line during the manufacture of a layer (for example during the extrusion of the layer), the target layers (4) shown in FIG. 2 would continually be replaced by new target layers as the layered structure is moved past the place of illumination.

Figure 3:
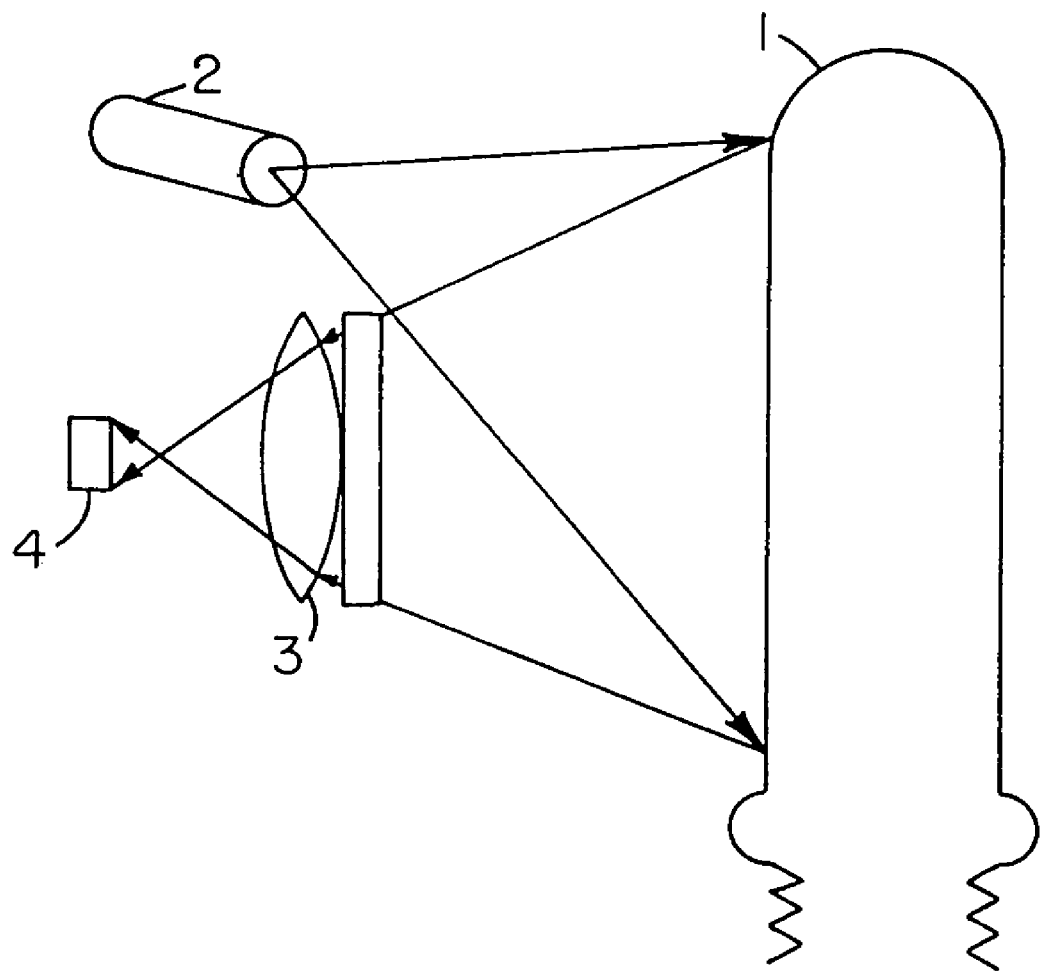
FIG. 3 depicts a preferred embodiment of apparatus which is suitable for measuring the thickness of layers in a molded article, such as a preform or container.

FIG. 3 shows a preferred embodiment of another apparatus useful for the inspection of one or more layers of a plastic bottle or a plastic preform that can later be molded into a bottle. In this embodiment a light source with associated optical system (2) is used to project light onto the preform or bottle (1) in such a manner as to produce a line of light on the preform or bottle. This light induces fluorescence in the layer containing the fluorophore compounds. An optical system (3) consisting of lenses, optical filters and possibly polarisers is used to isolate the fluorescent light from the light emitted by the light source. The optical system (3) also produces an image of the fluorescence on a detector (4) that can spatially resolve the image from different parts of the bottle or preform. This detector may, for instance, be a linear or two dimensional charge-coupled device (CCD). The signal from the CCD would be sent to an electronic system that analyzes the signal. This signal analysis would then provide the level of the fluorescent signal from spatially resolved parts of the bottle or preform and would thus provide information about the uniformity of the layer containing the fluorophore compounds. To obtain information about the uniformity of the layer for the full 360° circumference of the preform or bottle, the embodiment can provide for a method of turning the preform or bottle about its axis. Alternatively, the components (2), (3) and (4) maybe mounted on a device capable of rotating them around the bottle or preform.

The light source may be a diode laser with a line generating optic. The line generating optics may be a system of refractive or holographic lenses that produces an essentially uniform line of light on the bottle or preform. Alternatively, the line of light may be produced by a rotating or oscillating mirror that at any one instance would only illuminate a single spot but over a period of its rotation or oscillation would illuminate a line. Such optical systems are commonly found in bar code scanning equipment that uses a laser as the light source. The light source B may also consist of one or more light emitting diodes (LEDs) to relatively uniformly illuminate the portion of the bottle or preform that is to be inspected. Furthermore, incandescent lamps such as standard tungsten or halogen lamps may also be used. These would require optical filters to remove those wavelengths from their spectrum that would overlap with the emission spectrum of the fluorophore compounds.

For some applications it may be convenient to use a detector that does not have spatial resolution, such as a single photodiode, photomultiplier tube or avalanche photodiode. In this case, the optical system (3) would incorporate an oscillating or rotating mirror to focus fluorescent light from different portions of the bottle or preform onto the detector at different times. Systems of this type are again commonly found in certain bar code scanning equipment.

It should be realized that the particular apparatuses shown in FIG. 1, FIG. 2, and FIG. 3 are merely examples of apparatuses using inventive principles of the present invention. Having been taught principles of the present invention, those skilled in the art can easily see other apparatuses to accomplish the principles of the invention. For example, imaging systems could be used to interrogate a large plane target area. Hence, the apparatuses shown in the figures are illustrative and do not limit the invention.

Certain aspects of the invention are also illustrated by the following examples. Although the examples illustrate the invention, they do not express every aspect of the invention, and do not limit the invention.

EXAMPLE 1

A NIR fluorophore compound was copolymerized into a sodiosulfopolyester (0.09 mole fraction 5-sodiosulfoisophthalic acid, 0.41 mole fraction isophthalic acid, 0.23 mole fraction cyclohexanedimethanol, 0.27 mole fraction diethylene glycol) at 5000 ppm. The NIR fluorophore compound was Pc-AlOC6H3(CO2CH3)2, where Pc is phthalocyanine.

A total of 90 grams of this copolymer was compounded into 4.445 kilograms of a poly[ethylene terephthalate] (PET) copolyester containing 32 mole % 1,4-cyclohexanedimethanol on a 30 mm twin screw extruder to generate a 98.8 ppm NIR fluorophore first concentrate.

A total of 226.8 grams of this first concentrate were physically mixed with 1179 grams of a second concentrate and 3130 grams of the PET copolyester to form a composition having about 4.94 ppm NIR fluorophores. (The second concentrate contained 3.2 wgt % benzoxazinone [a UV absorber] and 96.8 wgt % the PET copolyester.) The resultant mixture was extruded to form a thin target layer through a 1" Killion extruder at screw speeds ranging from 10 to 90 RPM. The main extruder (a 2.5 inch MPM) was extruding unmodified PET copolyester to form a bulk layer at a screw speed ranging from 45 to 50 RPM's. Both these melt streams were brought together into a multilayer film in an AB coextrusion block, and extruded through a coat-hanger die. The extrudate was then cooled on polished rolls to form the multilayer film product. The main extruder screw speed was adjusted to maintain the thickness of the multi-layer film product at 0.118".

These coextruded layers were sectioned and imaged off-line by epi-fluorescence microscopy techniques to determine the thickness of the target layer ("Measured Thickness" in Table 1) using visible light (to excite the fluorophore) and the corresponding fluorescence signal was selected by filters and sent to the eyepiece or detector. Additional details concerning the technique used in this example are described in Chapter 8 Volume 1 of *Fluorescence Microscopy* by F. D. Roast and published by Cambridge University Press in 1992.

Figure 4:
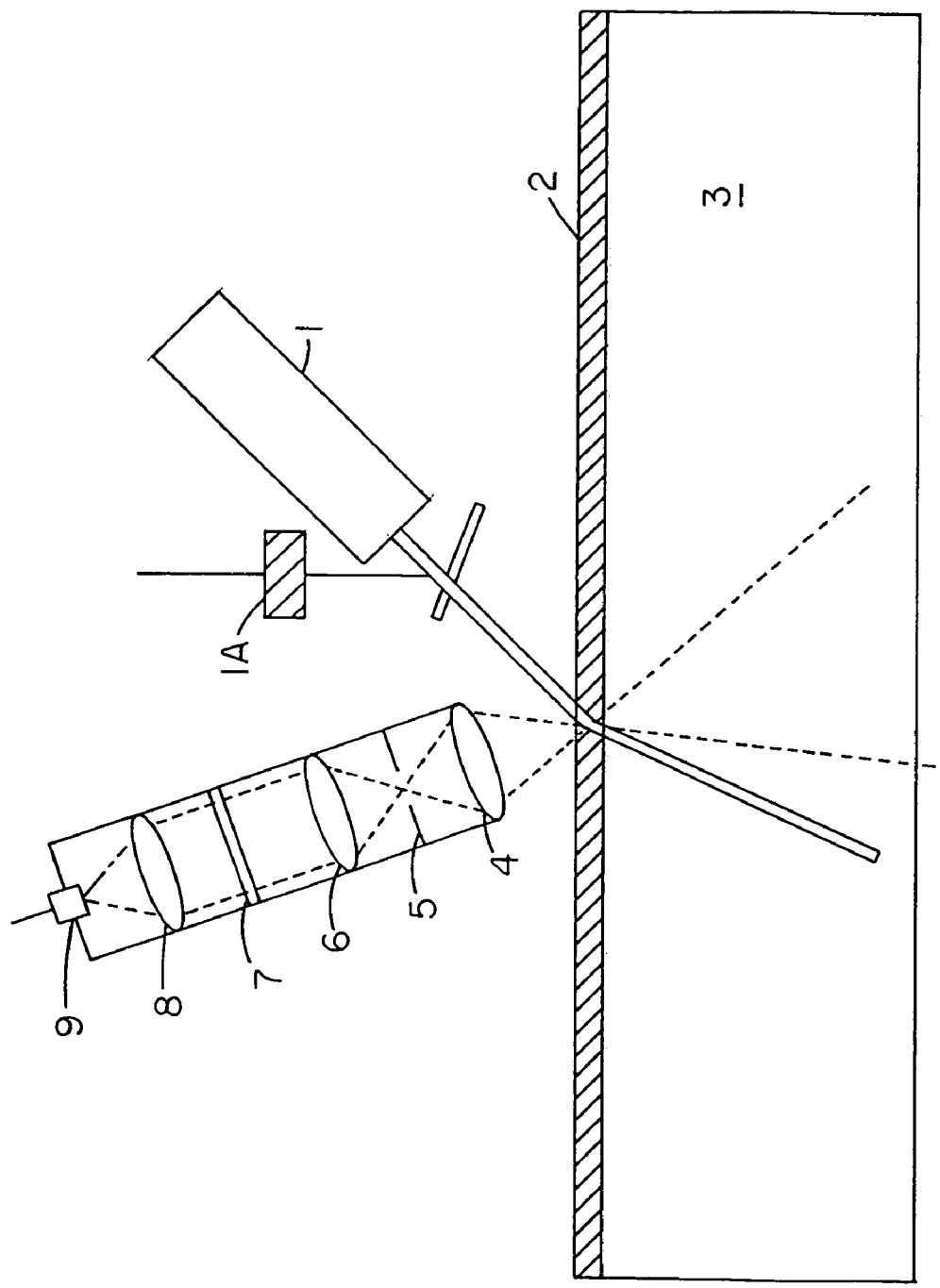
FIG. 4 depicts an instrument used in Examples 1 and 2 to make measurements to determine layer thickness.

These coextruded layers were also measured with an instrument suitable for on-line measurement. This instrument was assembled from readily available parts (e.g. from the Edmund Scientific Optical Components Catalog). A schematic of the instrument is shown in FIG. 4. For these measurements, a 670 nm diode laser (1) (with a controlling photodiode detector (1A)) was used to illuminate the target layer (2), which is attached to the bulk layer (3), and excite the NIR fluorophores in the target layer. The fluorescence signal was captured by the condenser lens (4), passed through an aperture (5), collimated by a lens (6), selected by a 730 nm interference filter (7), and focused by lens (8) on a silicon photodiode detector (9). The current from this photo-diode detector was measured by a Keithley current meter. Each sample was measured three times with this technique, and the current (nanoamperes) for each measurement is listed in Table 1.

TABLE 1

| Fluoroph conc. (ppm) | Satellite Extruder (RPM) | MPM Extruder (RPM) | layer Thickness (mils) | current (nA) Test 1 | current (nA) Test 2 | current (nA) Test 3 |
|---|---|---|---|---|---|---|
| 4.94 | 60 | 45 | 7.6 | 0.181 | 0.173 | 0.182 |
| 4.94 | 30 | 48 | 2.8 | 0.083 | 0.071 | 0.073 |
| 4.94 | 90 | 44 | 11.3 | 0.3 | 0.293 | 0.309 |
| 4.94 | 30 | 47 | 3.3 | 0.072 | 0.075 | 0.071 |
| 4.94 | 20 | 49 | 2.2 | 0.056 | 0.048 | 0.047 |
| 4.94 | 60 | 46 | 7.5 | 0.2 | 0.199 | 0.202 |
| 4.94 | 10 | 50 | 1.2 | 0.035 | 0.027 | 0.027 |
| 4.94 | 30 | 48 | 3.7 | 0.11 | 0.103 | 0.102 |
| 4.94 | 10 | 47 | 1.3 | 0.035 | 0.033 | 0.033 |
| 4.94 | 20 | 48 | 2.4 | 0.06 | 0.067 | 0.061 |

Figure 5:
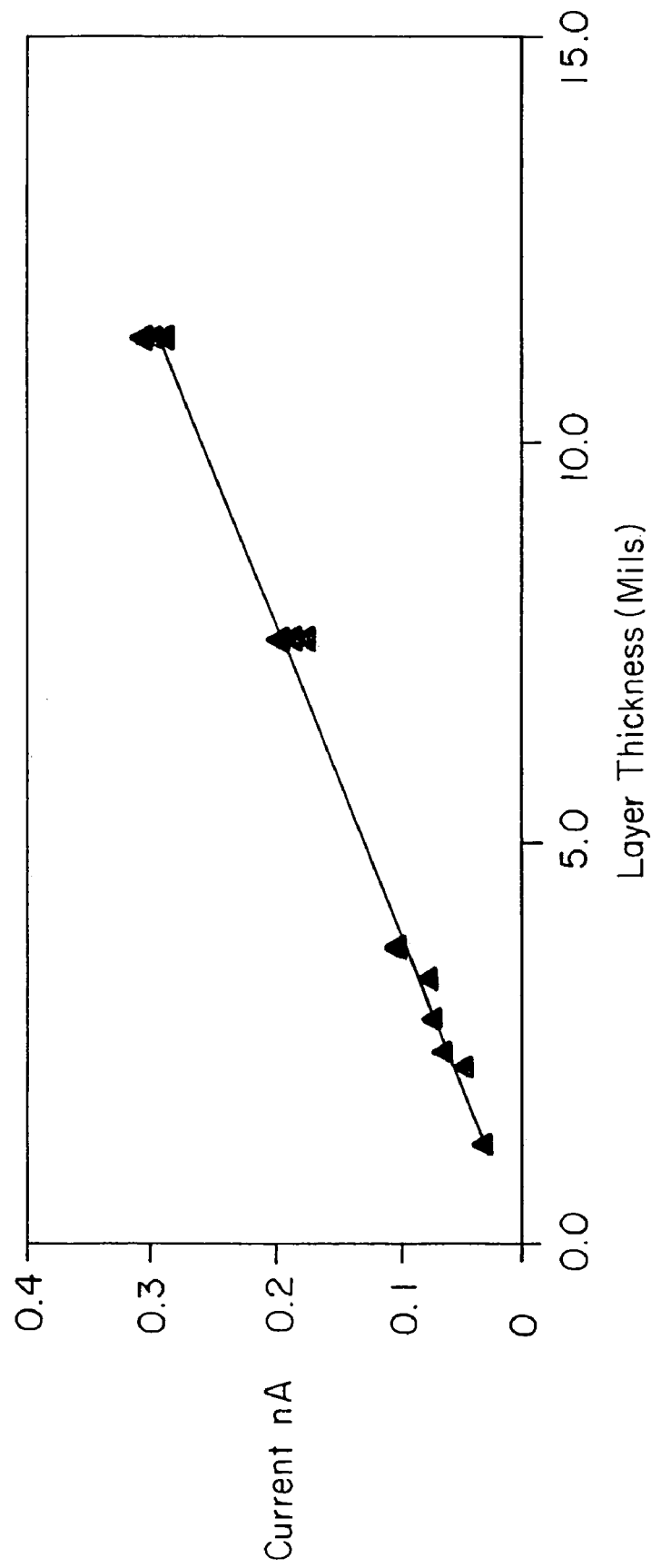
FIG. 5 depicts the correlation of fluorescent signal measured in Example 1.

Data from Table 1 is plotted in FIG. 5. The actual data is shown as the points, while the best fit of the data is shown as the line. The best fit of the fluorescence signal versus layer thickness had a correlation coefficient ($R^2$) of 0.99. The signal appears to be substantially linear with layer thickness.

EXAMPLE 2

The experiment was carried out in the same manner as in Example 1, except the NIR fluorophore concentration in the target layer was about half the concentration of Example 1. Specifically, the layers were made of the same materials and quantities as in example 1, except only 113.4 grams (as opposed to 226.8 grams in Example 1) of the first concentrate were physically mixed the second concentrate and the PET copolyester. The results from Example 2 are listed in Table 2.

TABLE 2

| Fluoroph conc (ppm) | Satellite Extruder (RPM) | MPM (RPM) | Fluoroph layer (mils) | current (nA) Test 1 | current (nA) Test 2 | current (nA) Test 3 |
|---|---|---|---|---|---|---|
| 2.47 | 60 | 46 | 7.4 | 0.12 | 0.125 | 0.108 |
| 2.47 | 20 | 48 | 2.6 | 0.055 | 0.049 | 0.044 |
| 2.47 | 30 | 48 | 3.9 | 0.071 | 0.065 | 0.061 |
| 2.47 | 10 | 50 | 1.3 | 0.022 | 0.023 | 0.018 |
| 2.47 | 30 | 48 | 3.8 | 0.046 | 0.052 | 0.046 |
| 2.47 | 20 | 49 | 1.4 | 0.026 | 0.033 | 0.035 |
| 2.47 | 10 | 50 | 1.2 | 0.021 | 0.022 | 0.019 |

Figure 6:
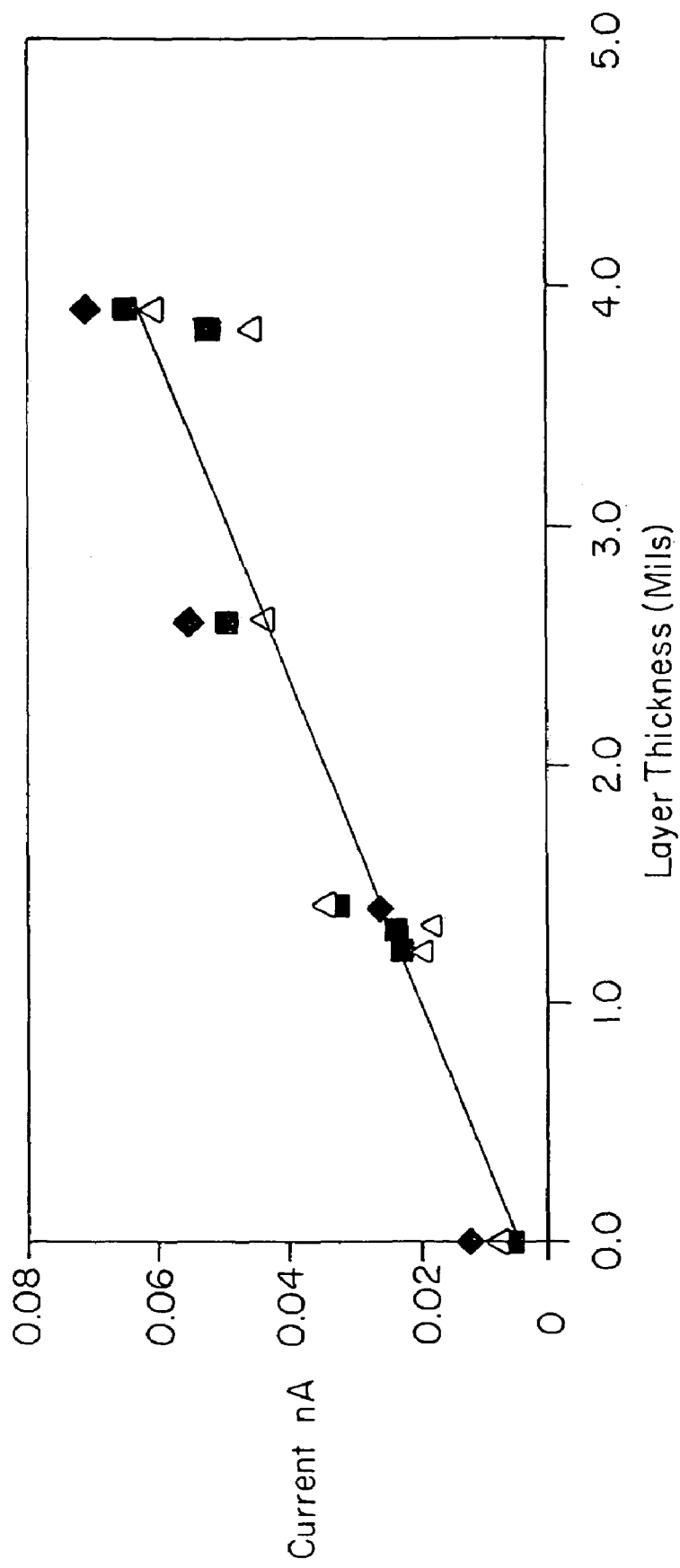
FIG. 6 depicts the correlation of fluorescent signal measured in Example 2.

Data from Table 2 is plotted in FIG. 6. The actual data is shown as the points, while the best fit of the data is shown as the line. The best fit of the fluorescence signal versus layer thickness had a correlation coefficient ($R^2$) of 0.96. The signal appears to be substantially linear with layer thickness.

We claim:
1. A method comprising:
   a. forming an article comprising a layer of a polymer composition comprising a known concentration and a substantially uniform distribution of one or more fluorophores that fluoresce at near infrared wavelengths, wherein the fluorophores are copolymerized with the polymer composition;
   b. exposing the layer to electromagnetic radiation to create a fluorescent signal; and
   c. measuring the fluorescent signal to determine the thickness of the layer.

2. The method according to claim 1, wherein the layer comprises a film.

3. The method according to claim 1, wherein the article comprises a preform.

4. The method according to claim 3, further comprising making a container from the preform.

5. The method according to claim 1, 2, or 3 wherein the polymer composition is selected from the group consisting of polyesters.

6. The method according to claim 5, wherein the exposing and measuring occur on-line immediately following or simultaneously with the forming of the article.

7. The method according to claim 1, 2 or 3, wherein the article further comprises at least one additional layer.

8. The method according to claim 7, wherein the additional layers independently comprise at least one material selected from the group consisting of polyesters, polyolefins, vinyl polymers, polycarbonates, polyurethanes, polysulfones, polyethers, polyacetals, polyacrylates, polyamides, polyimides, polyester-amides, polystyrenes, copolymers thereof, and non-polymeric waxes.

9. The method according to claim 7, wherein the thickness of the at least one additional layer is also determined.

10. The method according to claim 1, wherein the article is formed by a process selected from the group consisting of extrusion, co-extrusion, injection blow molding, co-injection blow molding, extrusion blow molding, co-extrusion blow molding, stretch blow molding, solution coating, spin blowing, lamination processes, injection molding, co-injection molding, and combinations thereof.

11. The method according to claim 1 wherein the polymer composition is selected from the group consisting of polyesters, polyolefins, vinyl polymers, polycarbonates, polyurethanes, polysulfones, polyethers, polyacetals, polyacrylates, polyamides, polyimides, polyester-amides, polystyrenes, and copolymers thereof.

12. The method according to claim 1, wherein the fluorophores comprise at least one material selected from the group consisting of phthalocyanines, naphthalocyanines, squaraines, carbocyanines, and zethrens.

13. The method according to claim 1, wherein the electromagnetic radiation is in a wavelength range selected from the group consisting of near infrared, ultraviolet, and visible.

14. The method according to claim 1, wherein the article comprises a container.

15. The method according to claim 1, wherein the layer comprises at least one polyamide.

16. The method according to claim 15, wherein the layer further comprises passive and/or active barrier enhancing compounds.

17. The method according to claim 16, wherein said passive barrier enhancing compounds comprise dispersed platelet particles and said active barrier enhancing compounds comprise oxygen scavenging compounds.

18. A method comprising:
   a. forming an article comprising a layer of a polymer composition comprising a known concentration and a substantially uniform distribution of one or more fluorophores that fluoresce at near infrared wavelengths, wherein the fluorophores are copolymerized with the polymer composition;
   b. exposing the layer to electromagnetic radiation to create a fluorescent signal; and c. measuring the fluorescent signal to determine non-uniformity of thickness of the layer.

19. The method according to claim 18, wherein the layer comprises a film.

20. The method according to claim 18, wherein the article comprises a preform.

21. The method according to claim 20, further comprising making a container from the preform.

22. The method according to claim 18, 19, or 20, wherein the polymer composition is selected from the group consisting of polyesters.

23. The method according to claim 18, 19 or 20, wherein the article further comprises at least one additional layer.

24. The method according to claim 23, wherein the additional layers independently comprise at least one material selected from the group consisting of polyesters, polyolefins, vinyl polymers, polycarbonates, polyurethanes, polysulfones, polyethers, polyacetals, polyacrylates, polyamides, polyimides, polyester-amides, polystyrenes, copolymers thereof, and non-polymeric waxes.

25. The method according to claim 23, wherein at least one additional layer comprises a known concentration and a substantially uniform distribution of at least one second fluorophore different from the fluorophore in the layer, further comprising the steps of exposing the additional layer to electromagnetic radiation to create a fluorescent signal; and measuring the fluorescent signal to determine thickness of the additional layer.

26. The method according to claim 18, wherein the article is formed by a process selected from the group consisting of extrusion, co-extrusion, injection blow molding, co-injection blow molding, extrusion blow molding, co-extrusion blow molding, stretch blow molding, solution coating, spin blowing, lamination processes, injection molding, co-injection molding, and combinations thereof.

27. The method according to claim 18, wherein the polymer composition is selected from the group consisting of polyesters, polyolefins, vinyl polymers, polycarbonates, polyurethanes, polysulfones, polyethers, polyacetals, polyacrylates, polyamides, polyimides, polyester-amides, polystyrenes, and copolymers thereof.

28. The method according to claim 18, wherein the fluorophores comprise at least one material selected from the group consisting of phthalocyanines, naphthalocyanines, squaraines, carbocyanines, and zethrens.

29. The method according to claim 18, wherein the electromagnetic radiation is in a wavelength range consisting of near infrared, ultraviolet, and visible.

30. The method according to claim 18, wherein the exposing and measuring occur on-line immediately following or simultaneously with the forming of the article.

31. The method according to claim 18, wherein the article comprises a container.

32. A method for making an article comprising a layer of a polymer composition comprising a known concentration and a substantially uniform distribution of one or more fluorophores that fluoresce at near infrared wavelengths, wherein the fluorophores are copolymerized with the polymer composition, the method comprising:
   a. exposing the layer to electromagnetic radiation to create a fluorescent signal;
   b. measuring the fluorescent signal; and
   c. using the fluorescent signal to control the thickness of the layer.

* * * * *